（12）United States Patent
Borodulin et al.

(10) Patent No.: US 7,654,953 B2
(45) Date of Patent: Feb. 2, 2010

(54) UNIVERSAL VAGINAL SPECULUM WITH DISCONNECTABLE BLADES

(76) Inventors: German Borodulin, 583 -46$^{th}$ Ave., San Francisco, CA (US) 94121; Ananias Diokno, 480 Hill Spur Rd., Ann Arbor, MI (US) 48105; Alexander Shkolnik, 485 Dartmouth Ave., San Carlos, CA (US) 94070

( * ) Notice: Subject to any disclaimer, the term of this patent is extended or adjusted under 35 U.S.C. 154(b) by 78 days.

(21) Appl. No.: 11/513,579

(22) Filed: Aug. 31, 2006

(65) Prior Publication Data

US 2006/0293567 A1 Dec. 28, 2006

Related U.S. Application Data

(63) Continuation of application No. 09/565,613, filed on May 4, 2000, now Pat. No. 6,379,299, and a continuation of application No. 09/977,029, filed on Oct. 15, 2001, now Pat. No. 6,569,091.

(51) Int. Cl.
  *A61B 1/32* (2006.01)
(52) U.S. Cl. .................. 600/220; 600/222; 600/213
(58) Field of Classification Search ................ 600/220, 600/476, 235, 190, 184, 222, 219, 196, 201, 600/210, 214, 213
  See application file for complete search history.

(56) References Cited

U.S. PATENT DOCUMENTS

| 2,579,849 | A | * | 12/1951 | Newman | 600/215 |
| 3,716,047 | A | * | 2/1973 | Moore et al. | 600/212 |
| 3,762,400 | A | * | 10/1973 | McDonald | 600/212 |
| 3,851,642 | A | * | 12/1974 | McDonald | 600/212 |
| 6,379,299 | B1 | | 4/2002 | Borodulin et al. | |
| 2005/0043633 | A1 | * | 2/2005 | Marcotte | 600/476 |
| 2005/0124860 | A1 | | 6/2005 | Mohajer | |
| 2008/0004497 | A1 | * | 1/2008 | Whitehead et al. | 600/184 |

FOREIGN PATENT DOCUMENTS

WO WO 2005/055819 6/2005

* cited by examiner

*Primary Examiner*—Pedro Philogene (57) ABSTRACT

A vaginal speculum having a handle portion and a set of blade pairs some of which can be removably attached to the distal end of the handle and others can be slidingly inserted through the proximal end of the handle. Both pairs of the blades have snapping engagement with one and the same locking mechanism of the handle. The handle may constitute a permanent part, and the blades may be replaceable.

8 Claims, 5 Drawing Sheets

UNIVERSAL VAGINAL SPECULUM WITH DISCONNECTABLE BLADES

REFERENCES TO RELATED APPLICATIONS

The present patent application is a continuation application of U.S. patent application Ser. No. 09/565,613 filed on May 4, 2000 (now U.S. Pat. No. 6,379,299 issued on Apr. 30, 2002) and of U.S. patent application Ser. No. 09/977,029 field on Oct. 15, 2001 (now is U.S. Pat. No. 6,569,091 issued on May 27, 2003), both aforementioned patent applications being filed by the same applicants.

BACKGROUND OF THE INVENTION

1. Field of the Invention

The present invention relates to medical diagnostic instruments, in particular to a vaginal speculum for visual examination of the vaginal cavity, vaginal walls, and conditions of the cervix.

2. Description of the Related Art

A vaginal speculum is a diagnostic instrument for dilating the opening of the vagina cavity in order that the interior may be more easily visible for observation. A vaginal speculum has two expandable blades, which are inserted into the vagina in a closed state and then expanded, or moved apart for dilating the vaginal cavity. In particular, a vaginal speculum is an indispensable instrument not only for gynecologists but also for primary care physicians, geriatricians, urologists, and nurse practitioners for urological examination of patients suffering from urinary incontinence in order to exclude the presence of vaginal prolapses, such as rectocele, cystocele, enterocele, and uterine prolapse. Vaginal prolapses of the aforementioned type are protrusions or herniation of the urethra or other pelvic organs into the vagina.

One typical vaginal speculum is described in U.S. Pat. No. 3,716,047 issued in 1973 to W. C. Moore et al. . The instrument consists of three parts of molded non-toxic plastic materials, i.e., a fixed member, a movable member, and a sliding member. The sliding member is slidingly installed in the fixed member and pivotally supports the movable member so that the movable member can be rotated around the pivot at the proximal end of the fixed member. As a result, the distal ends of the movable and fixed members, which form expandable blades insertable into the vagina, can dilate the vagina cavity and thus allow internal vaginal observations. The members are made from a transparent plastic, and the blades form a hollow thin-wall body of a circular or oval cross-section, which allows the observation.

A procedure of examination of a vagina with the use of a speculum involves movements of the speculum in an expanded, i.e., an outwardly diverging state in the direction towards or away from the uterus. This is necessary for diagnosing aforementioned vaginal prolapses. However, since the opening of the vagina has a circular muscle, which is more resistant to dilations than the vaginal cavity, the aforementioned withdrawal of the expanded speculum may cause in patient discomfort and painful sensations. This is because in the course of the withdrawal of the speculum the diameter of its portion at the vaginal opening is stretched by the speculum. Furthermore, the conventional vaginal specula do not have features for measuring the length of vagina and for testing and measuring the severity of the prolapses without completely removing the entire speculum. Normally, the physician disassembles the speculum and inserts only one of the blades for pressing on one wall of the vagina for exposing and observing the opposite wall. In case of prolapses, a separate ruler is used for measuring the length and position of the prolapse or prolapses. The procedure is then repeated for expositing the opposite wall of the vagina cavity. In some cases, the physician uses a separate single metal blade for pressing on the anterior and posterior walls of the vagina cavity. Thus, the examination involves the use of several tools, as well as assembling and disassembling operations. Thus, it is impossible with conventional specula to conduct more concentrated and localized examination of one wall of the vaginal cavity without removing the entire speculum from the vagina.

The speculum of U.S. Pat. No. 3,716,047, as most other of known specula, is of the type that is discarded after use. This results in a significant waste of plastic materials and creates a burden for the environment. A gynecologist can often use twenty of these instruments per day of work and, accordingly. Therefore, in addition to the excessive waste of plastics material, this becomes costly to the physician. It also requires excessive storage space in the examination room.

The above problems have been solved by the applicants who developed a disposable vaginal specula with adjustable and removable blades. One of these vaginal specula is disclosed in U.S. Pat. No. 6,379,299 issued on Apr. 30, 2002 to G. Borodulin, et al. and another in U.S. Pat. No. 6,569,091 issued on May 27, 2003 to G. Borodulin et al. that is a another modification of the speculum with adjustable and removable blades.

As in a conventional device, the each of the aforementioned specula consists of two blades pivotally interconnected through a fork-like member so that the blades can be expanded and fixed in an expanded state in order to dilate the vagina for observing the condition of the vagina cavity. However, in contrast to a conventional three-piece speculum, the devices of U.S. Pat. No. 6,379,299 and U.S. Pat. No. 6,569,091 have blades consisting of axially extended handle parts and moveable parts that form distal ends of the blades and can be withdrawn partially or completely from the handle parts for replacement with blades of other dimensions without withdrawing the entire speculum from the vagina. Provision of retractable blades makes it possible for a physician to withdraw the moveable parts of the blades in an alternating sequence for exposing one of the walls of the vagina cavity by pressing down with the longer blade on the opposite wall.

In an assemble state of the speculum, the aforementioned handle parts form a handle of the speculum. In fact, the handle that consists of two handle portions and the slider with the blade pivoting mechanism may not be discarded and reused. This is because the distal ends of the aforementioned handle portions that extend in the axial direction of the moveable portions of the blades are used for guiding the moveable portions and not inserted into vagina of a patient during the use of the speculum, and only the moveable parts that extend in the distal direction from the handle portions are intended for the insertion. Thus, after slight sanitary treatment, e.g., by dipping into an appropriate solution or by wiping, the handle portion, slider, and pivoting mechanism can be reused. If necessary, the handle portion can be made of a sterilizable plastic or metal.

Another attempt to provide a vaginal speculum with a re-usable handle is described in published U.S. Patent Application No. 20050043633 filed on Aug. 19, 2003 by Marcotte, Jacques R. This publication describes a vaginal speculum with a permanent handle and replaceable blades. Each blade is attached to the distal or front end of the respective handle parts by means of a circular ridge on the handle portion and conforming circular groove on the inner surface of the blade. For connection, the ridge is inserted into the groove and is pressed into it for fixation by snapping. For disconnection, it is sufficient to twist the blade out of the engagement.

As compared to the device of U.S. Patent Application No. 20050043633, the specula of U.S. Pat. Nos. 6,379,299 and 6,569,091 allow not only the multiple use of the handle but also installation of the blades in any convenient position due to the sliding engagement of the blades with the handle parts. For example, one of the blades can be retracted and expose one of the vaginal walls for observation of prolapses.

Nevertheless, in both cases, i.e., in the case of the specula of U.S. Pat. Nos. 6,379,299, 6,569,091, and U.S. Patent Application No. 20050043633, the handle is suitable for multiple usage with disposable blades, thus providing significant saving of plastic materials, reducing the space required for storage of the specula, and reducing the impact on the environment. However, in the specula of all aforementioned types the front or distal ends of the handle parts are not protected from contact, at least with the patient's genitalia. This increases a risk of infecting the front ends of the speculum handle that is intended for multiple usage and may require addition measures for aseptic treatment of the handle.

SUMMARY OF THE INVENTION

It is an object of the present invention to provide a universal vaginal speculum with a multiple-usage handle and disposable removable blades, where the blades provide protection of the handle front parts from contact with the patient's body and from possibility of infecting. It is another object to provide a universal vaginal speculum of the aforementioned type that can be used either with removable blades connectable without movements relative to the handle or with blades that can be slidingly connected to the handle or with one of the blades completely removed from the handle without removing the entire speculum from the patient's vagina. Still another object is to provide a vaginal speculum of the aforementioned type with means for protecting the interior of the front parts of the handle from penetration of vaginal discharge, or the like.

In general, the vaginal speculum of the present invention is the same as the one disclosed in U.S. Pat. No. 6,379,299 of the same applicants and differs from it by being additionally provided with removable blades having means for protecting the front parts of the handle from contact with the patient's body, e.g., with the patient's genitalia. More specifically, each blade has a distal portion insertable into the patient's vagina and a proximal portion that is made in the form of a protective hood over the front part of the handle and is telescopically fitted onto its outer surface. The proximal end of each of the blades is made in the form of two concentric semi-circular parts. When the blade is telescopically fitted onto the distal ends of the respective handle part, the outer semi-circular part slides over the outer surface of the distal end of the handle part, while the inner semi-circular part slides over the inner surface of the distal end of the handle part. The outer surface of the inner semi-circular part has a detent, while the inner surface of the distal end of the handle part has a respective dimple or a through opening for snapping engagement with the detent and thus for removably securing the blade to the handle. In order to provide the snapping action, the detent is formed on a flexible lobe or tab formed by making a U-shaped cutout around the detent so that during the snapping action the tab can be slightly bent inwardly due to resilient properties of the plastic material of the blade. In order to facilitate connection and disconnection of the blade, the side walls of the detent and dimple or opening may have tapered or rounded profiles. In fact, in the vaginal specula of U.S. Pat. Nos. 6,379,299 and 6,569,091 the aforementioned dimple or opening already exists on the inner semi-circular surface of the distal part of the handle portion for engagement with the detent of the removable and sliding blade. The difference is that in the specula of U.S. Pat. Nos. 6,379,299, 6,569,091 the blades are inserted for fixation into the speculum from the proximal end of the handle, while in the speculum of the invention the blade is inserted for fixation from the distal end, but in both cases the detent is snapped in the same dimple or opening. This means, that the specula of U.S. Pat. Nos. 6,379, 299 and 6,569,091 can be selectively used either with the blades slidingly guided in the handle and insertable through the proximal end of the handle or with the blades that are insertable from the distal end of the handle and provides the distal ends of the handle with additional hygienic protection. Furthermore, in order to prevent penetration of vaginal discharge into the interior of the distal end of the handle, the blades with protective hoods have, in the area of the protective hood, an inwardly projecting shoulders that are slightly raised above the longitudinal inner edges of the blade. In order to prevent interference between these shoulders in a completely closed state of the speculum, the shoulders on one of the blades may be provided with recesses for accommodating the edges of the mating shoulder on the other blade. In the specula of U.S. Pat. Nos. 6,379,299 and 6,569,091 similar protective shoulders are formed by blade guide portions of the handle parts.

DETAILED DESCRIPTION OF PRACTICAL EMBODIMENTS OF THE INVENTION

Figure 1:
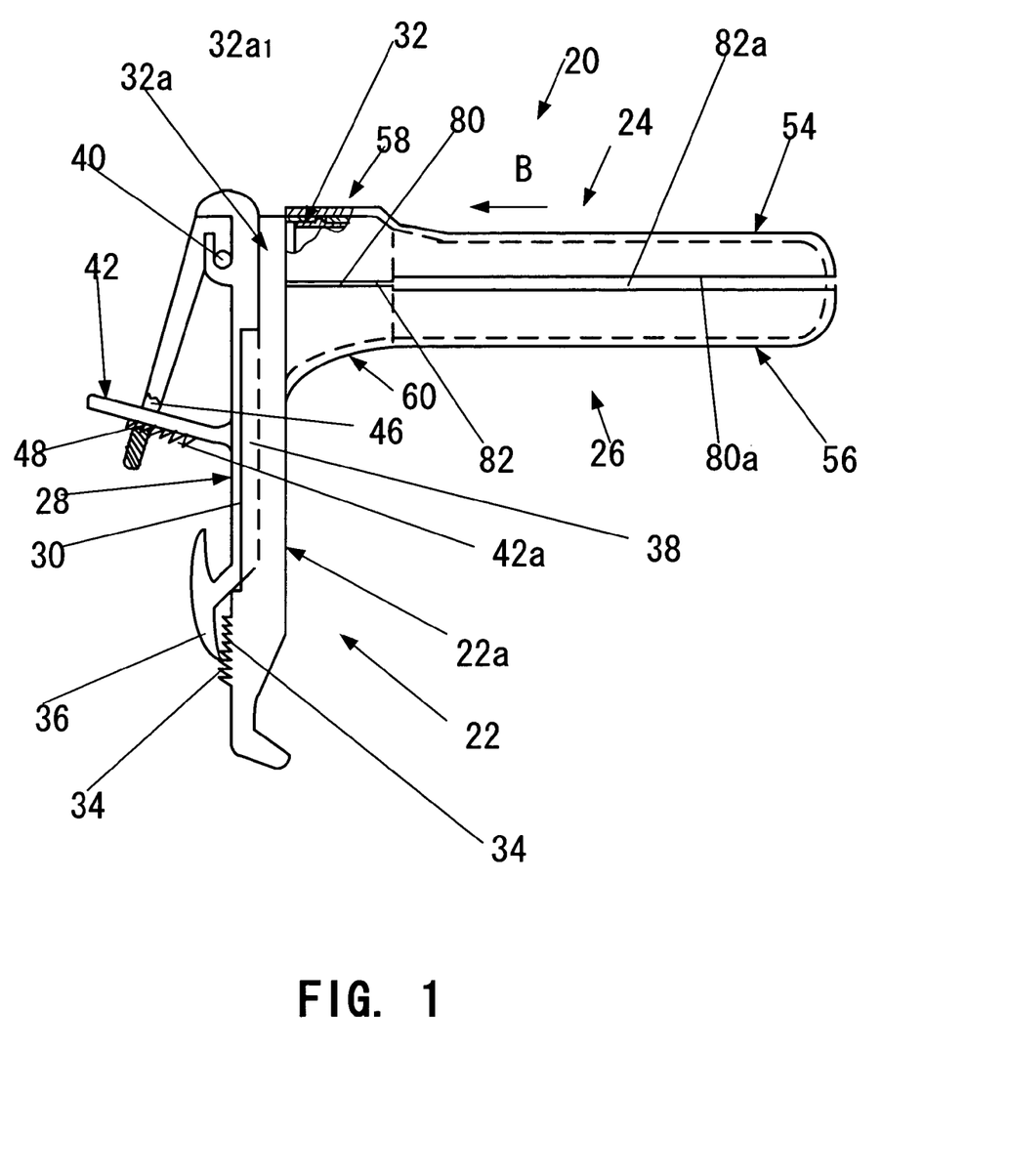
FIG. 1 is a general view of the vaginal speculum of the invention with multiple-usage handle that can be used in combination with replaceable blades that can be rigidly secured to the handle or with blades slidingly moveable and removable.

FIG. 1 is a general view of the vaginal speculum 20 of the invention with multiple-usage handle 22 that can be used in combination with replaceable blades 24 and 26 that can be rigidly secured to the handle 22 or with blades slidingly moveable and removable (shown and described below).

As a known vaginal speculum, e.g., of U.S. Pat. No. 6,379, 299, the speculum 20 consists of two disconnectable blades 24 and 26 that extend in the longitudinal directions parallel to the axis X-X and a fork-like slide 28 that can be moved in the transverse direction of the axis Y-Y substantially perpendicular to the axis X-X and is guided in a guide 30 formed on the rear side of the handle 22. The handle 22 consists of two parts, i.e., a lower handle part 22a that has an L-shaped configuration with a blade-attachment portion 22a, that is parallel to the axis X-X and a grip portion $22a_2$ that is parallel to the axis Y-Y, and an upper handle part 32 that also has an L-shaped configuration and consists of a blade-attachment front portion $32a_1$ parallel to the axis X-X and a rear portion $32a_2$ that, as shown in FIG. 1, extends downward from the blade 24 and rearward at a small angle from the grip portion $22a_2$.

The grip portion $22a_2$ has on its rear surface a tooth rack 34 with ratchet teeth. The slide 28 has a pawl 36 on its lower end for engagement with the teeth of the tooth rack 34 in a pawl-ratchet manner. The upper end of the slide 28 is made in the form of a U-shaped fork with two parallel legs, only one of which 38 is seen and designated in FIG. 1. The legs of the fork embrace the upper handle part 32 and pivotally supports it on pins formed on the upper handle parts and inserted into openings or slots provided in the legs of the slide 32. Only one such pin 40 is seen in FIG. 1 while a similar pivot connection is available on the opposite side of the speculum 20.

The slide 28 has a rearward projection 42 substantially perpendicular to the axis Y-Y. The projection 42 has ratchet teeth 42a on its lower side, while the rear portion $32a_2$ of the upper handle part 32 is made with an oval-shaped opening 46 aligned with the opening formed between the legs of the U-shaped fork of the slide 28 and has a pawl 48 on the lower end of the oval-shaped opening 46 for engagement with the ratchet teeth 42a.

Figure 2:
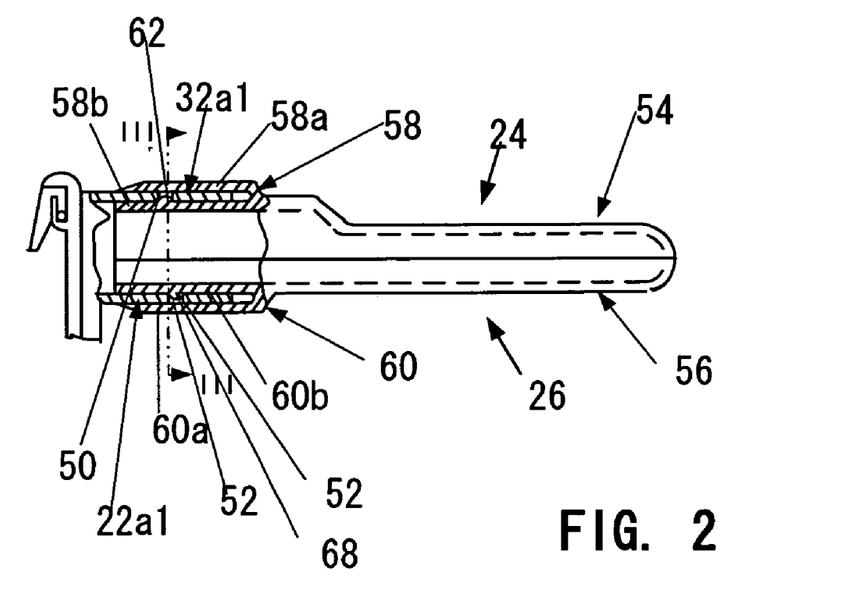
FIG. 2 is a fragmental longitudinal sectional view of the vaginal speculum of FIG. 1 with the mechanism of attachment of the blades.

FIG. 2 is a fragmental longitudinal sectional view of the vaginal speculum 20 with the mechanism of attachment of the blades 24 and 26. As in the specula of aforementioned U.S. Pat. Nos. 6,379,299 and 6,569,091, the blade-attachment portion $32a_1$ of the upper handle part 32 and the blade-attachment portion 22a, of the lower handle part 22a have on their inner surfaces dimples or openings 50 and 52, respectively.

All the structural elements described so far are exactly the same as respective structural elements of the vaginal specula disclosed in aforementioned U.S. Pat. Nos. 6,379,299 and 6,569,091 issued to the same applicants. Therefore, their details description and additional views (such as a rear view and top view that may show the shape of the aforementioned oval opening or pivotal connections on the side opposite to the one of FIG. 1) are omitted. The novel features reside in the blades that will now be described.

More specifically, as shown in FIG. 2, each blade 24 and 26 has a distal portion insertable into the patient's vagina and a proximal portion that is made in the form of a protective hood over the front part of the handle and is telescopically fitted onto its outer surface. In FIG. 2, the distal portion of the blade 24 is designated by reference numeral 54, and the distal portion of the blade 26 is designated by reference numeral 56. The proximal part of the blade 24 is designated by reference numeral 58, and the proximal part of the blade 26 is designated by reference numeral 60.

The proximal ends 58 and 60 of the blades 24 and 26, respectively, are made in the form of two concentric semicircular portions. The outer semicircular portion of the proximal end 58 is designated as 58a, and the inner semicircular portion of the proximal end 58 is designated as 58b. Similarly, the outer semicircular portion of the proximal end 60 is designated as 60a, and the inner semicircular portion of the proximal end 60 is designated as 60b (FIG. 2).

As can be seen from FIG. 2, in an assembled state of the vaginal speculum 20, i.e., in a state of the speculum with the blades 24 and 26 attached to the handle portions 32a and 22a, respectively (FIGS. 1 and 2), the proximal end 58 of the blade 24 is telescopically fitted onto the blade-attachment front portion 32a, (FIG. 1) of the upper handle part 32a, and the proximal end 60 of the blade 26 is telescopically fitted into the blade-attachment front portion $22a_1$ of the lower handle part 22a. In other words, as can be seen from FIG. 3, which is a cross section along the line III-III of FIG. 2, the radial distance between the outer semicircular portion 58a and the inner semicircular portion 58b corresponds to the wall thickness of the blade-attachment front portion 22a, with the dimensions that provide a sliding fit between the mating parts of the proximal end 58 of the blade 24 and the blade-attachment front portion 32a, of the upper handle part 32a. Similarly, the radial distance between the outer semicircular portion 60a and the inner semicircular portion 60b corresponds to the wall thickness of the blade-attachment front portion $22a_1$ with the dimensions that provide a sliding fit between the mating parts of the proximal end 60 of the blade 26 and the blade-attachment front portion 22a, of the lower handle part 22a.

It can be seen from FIGS. 1 and 2 that in an assemble state of the speculum 20, the blade-attachment front portions $32a_1$ and 22a, of the respective upper and lower handle parts 32a and 22a are completely covered with the proximal ends 58 and 60 of the respective blades 24 and 26.

Figure 4:
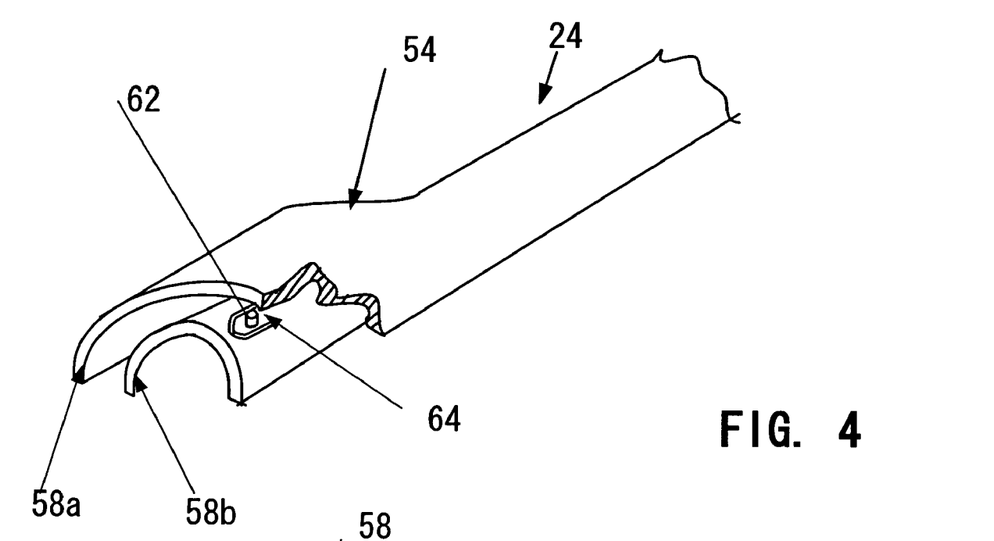
FIG. 4 is a perspective view of the upper blade with a part removed from the proximal end.
Figure 5:
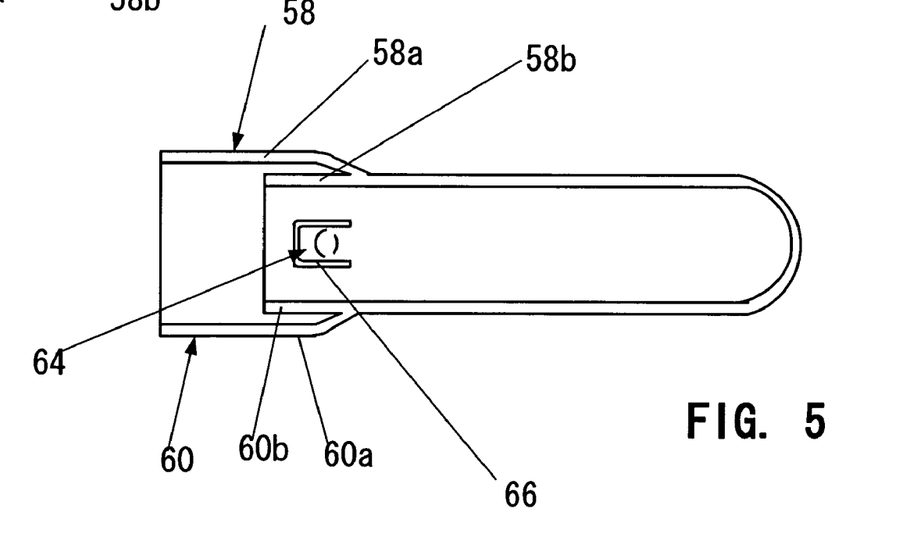
FIG. 5 is a view on the inner surface of the upper blade in the direction of arrow A.

FIG. 4 is a perspective view of the blade 24 with a part removed from the proximal end 58, and FIG. 5 is a view on the inner surface of the upper blade 24 in the direction of arrow A. As can be seen from FIGS. 4 and 5, the outer surface of the inner semi-circular part 58b has a detent 62 for insertion into the aforementioned dimple or a through opening 50 (FIG. 2) formed in the blade-attachment front portion 32a, of the upper handle part 32a. The detent 62 is intended for snapping in the opening 50, when the blade 54 is fitted onto the upper handle part 32a, and for unsnapping, when the blade 24 is disconnected from handle.

In order to provide the snapping/unsnapping action, the detent 62 is spring-loaded by being formed on a flexible lobe 64 formed by making a U-shaped cutout 66 (FIGS. 3 and 5) around the detent 62 so that during the snapping action the tab 64 can be slightly bent inwardly (into a position shown by the broken line 64a in FIG. 3) due to resilient properties of the plastic material of the blade 24. A similar mechanism is used for connection/disconnection of the blade 26 with the use of a detent 68 spring-loaded with the use of the lobe 70 formed by a cutout 72 (FIG. 3) in the inner semicircular part 60b. The detent 68 is intended for snapping engagement with the dimple or opening 74 formed in the blade-attachment front portion 22a, of the lower handle part 22a (FIG. 2).

Figure 6:
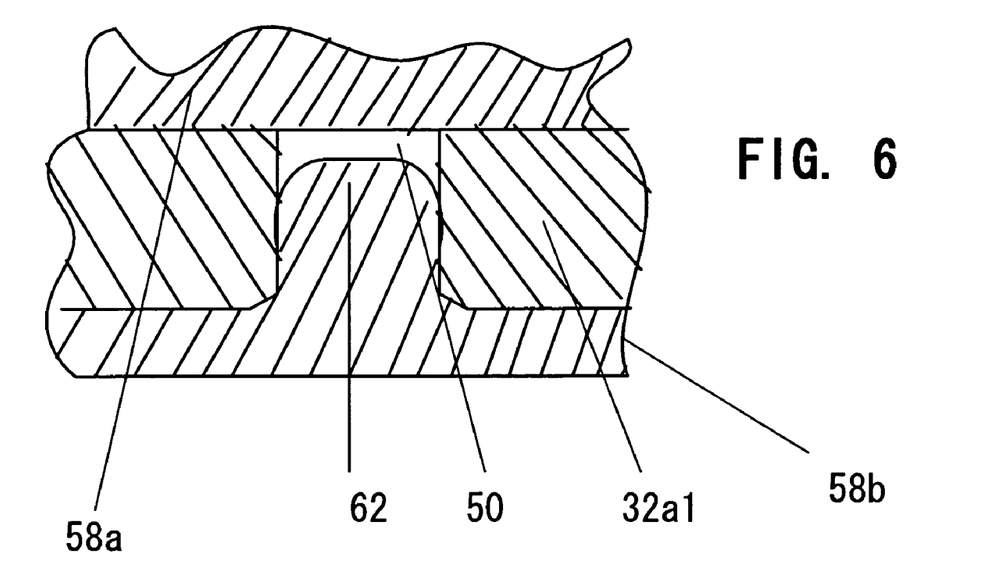
FIG. 6 is an enlarged fragmental view that illustrates profiles of the detent and opening.

The detent 62, opening 50 and the detent 68, opening 74 form blade locking mechanisms that are similar to those described in aforementioned U.S. Pat. No. 6,379,200. In fact, when the handle used for the blades 24 and 26 of the present invention is the same as in the vaginal speculum of U.S. Pat. No. 6,379,200, the dimples or openings already exist in the speculum handle and are ready for engagement with the detents 62 and 68 of the blades 24 and 26, respectively. In order to facilitate connection and disconnection of the blades 24 and 26, the side walls of the detents 62 and 68 and dimples or openings 50 and 74, respectively, may have tapered or rounded profiles, as shown in FIG. 6 for the upper blade 24.

Figure 3:
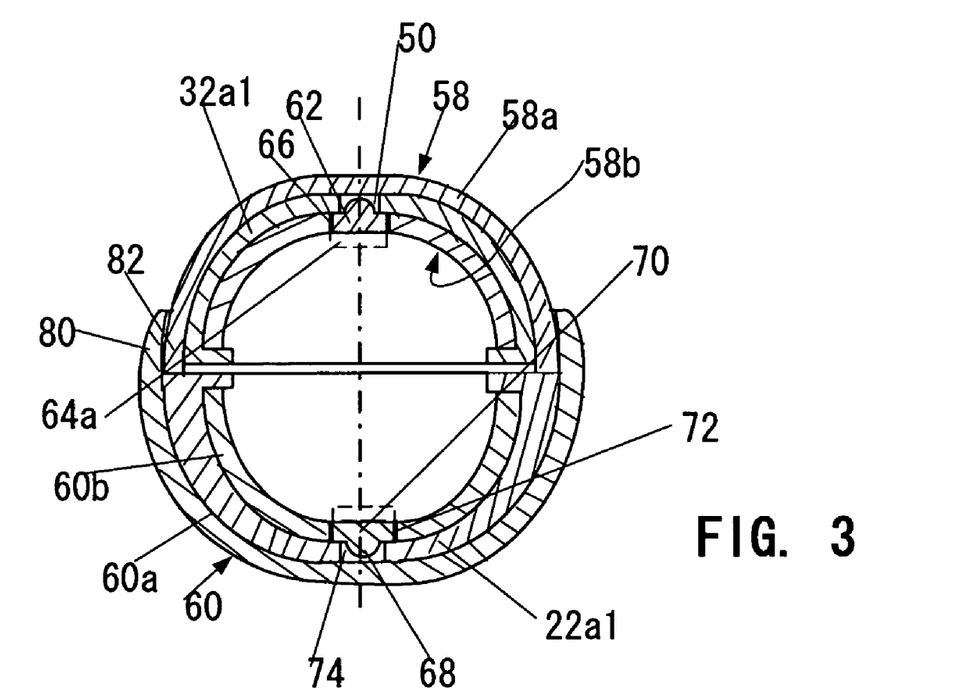
FIG. 3 which is a cross section along the line III-III of FIG. 2.

Furthermore, in order to prevent penetration of vaginal discharge into the interior of the lower handle part 22a and upper handle part 32a, the mating edges 80 and 82 (FIG. 1) on the proximal ends 58 and 60 of the blades 24 and 26, respectively, slightly projects above the longitudinal edges 80a and 82a of the respective blades 24 and 26, thus forming shoulders. As shown in FIG. 3, in order to prevent interference between these shoulders in a closed state of the blades, the shoulder 80 is formed with a recess for accommodating the shoulder 82. If necessary, the recess can be made in the shoulder 82 for accommodating the shoulder 80.

Figure 7:
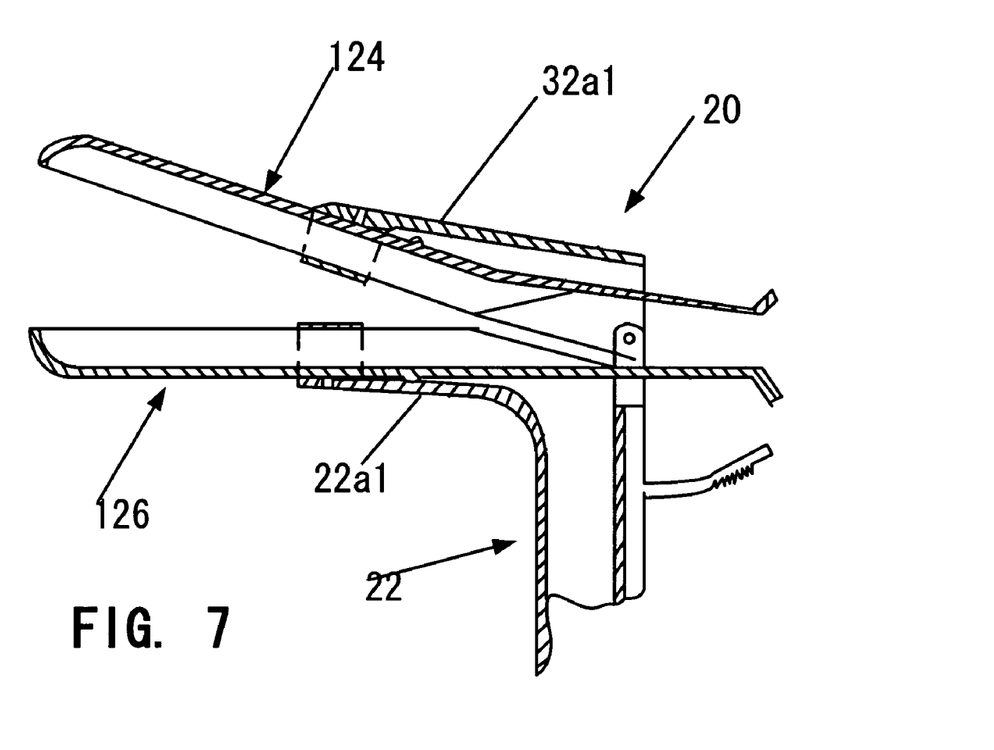
FIG. 7 is a longitudinal sectional view of the speculum of FIG. 1 with moveable blades inserted into the respective blade-attachment portions of the handle through the proximal end of the speculum.

In the specula of U.S. Pat. Nos. 6,379,299 and 6,569,091 similar protective shoulders already exist and are formed by blade guide portions of the handle parts. This is shown in FIG. 7, which is a longitudinal sectional view of the speculum 20 with moveable blades 124 and 126 inserted into the respective blade-attachment portions 32*a*, and 22*a*, respectively. It can be seen that the blade-attachment portions 32*a*, and 22*a*, of the handle of U.S. Pat. No. 6,569,091 already have the aforementioned dimples 50 and 52 in the respective handle portions 32*a* and 22*a*.

Prior to use, the multiple-usage handle 22 should be sterile or clean, and the blades 24 and 26 also should be sterile or clean and intended for discarding after single use.

The speculum 20 of the invention with multiple-usage handle 22 can be used as a conventional completely disposable vaginal speculum but with selection of the rigidly securable blades, such as the blades 24 and 26 shown in FIGS. 1-3, or with sliding blades 124 and 126 shown in FIG. 7. Opening of the blades and fixation in the selected position is carried out with the use of the ratchet mechanism 34-36 (linear displacement of the slide 28 in the direction of axis Y-Y) and the ratchet mechanism 42*a*-48 (angular displacement). In case of the blades 24 and 26, the proximal end 58 of the blade 24 is telescopically fitted in the direction of arrow B onto the blade-attachment front portion $32a_1$ (FIG. 1) of the upper handle part 32*a*, and the proximal end 60 of the blade 26 is telescopically fitted in the direction of arrow be onto the blade-attachment front portion $22a_1$ of the lower handle part 22*a*. As the blades 24 and 26 are shifted further towards the handle and their proximal end faces come into contact with the respective detents 62 and 68, the tabs 64 and 70 are resiliently bend inward, and the detents 62 and 68 are snapped in the opening or dimples 50 and 52, respectively. The vaginal speculum is then used in accordance with the required procedure, in which the distal portions 54 and 56 of the blades 24 and 26, respectively, are inserted into the patient's vagina, while the upper handle part 32*a* and lower handle part 22*a* are covered with the hood-like proximal ends 58 and 60 of the blades and thus prevented from contact with the patient's body. When the procedure is completed, the blades 24 and 26 are removed from the handle parts 32*a* and 22*a* by pulling the blades in the direction opposite to arrow B. The handle remains clean and can be reused after a slight sanitary treatment.

In case of the sliding blades 124 and 126, they are used in the same manner as described in U.S. Pat. No. 6,379,299.

Figure 8:
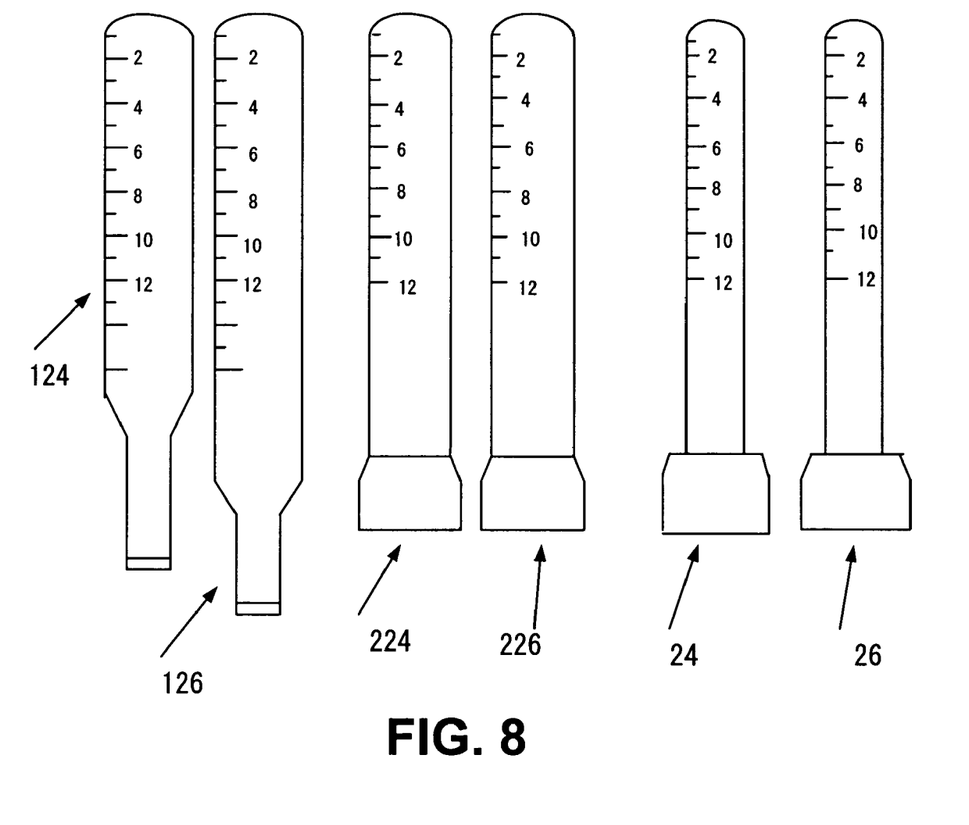
FIG. 8 is a view that illustrates an example of a set of blades suitable for use in conjunction with the multiple-usage handle of the invention.

The speculum 20 can be provided with a set of blades 24, 26 and 124,126 for use with the multiple-usage handle 22. Moreover, the blades attachable from the distal end, in turn, may comprise a set of blades different in width. FIG. 8 illustrates an example of a set of blades suitable for use in conjunction with the multiple-usage handle 22. It can be seen from FIG. 8 that the set may consist of the following blade pairs: 1) a pair of sliding blades 124 and 126 of the type shown also in FIG. 7 and intended for insertion into the handle 22 from the proximal end of the speculum handle; 2) a set of small-size non-moveable blades 24 and 26 attachable to the handle from the distal end of the handle 22; and 3) a set of medium-size non-moveable blades 224 and 226 attachable to the handle from the distal end of the handle 22. It is understood that the connection elements, i.e., the detents, of all blades of the set should be identical for snapping engagement with the same opening or dimple of the handle 22. It is understood that the pairs of attachable blades 24, 26 and 224, 226 may have not only different width but also different length. The pair of sliding blades 124 and 126 also may be replaced by blades of the same width but different length.

The entire vaginal speculum 20 can be made from the biologically acceptable plastic, or the handle can be made from acrylic plastic, metal, or any other suitable material, and the disposable blades can be made from polysterol or acrylic plastic. As in the case of U.S. Pat. Nos. 6,379,299 and 6,569, 091, the sliding blades 124 and 126 may have measurement scales for various measurements that may be required by the procedure.

Thus, it has been shown that the invention provides a universal vaginal speculum with a multiple-usage handle and disposable removable blades, where the blades provide protection of the handle front parts from contact with the patient's body and from possibility of infecting. The universal vaginal speculum of the invention can be used either with removable blades connectable without movements relative to the handle, or with blades that can be slidingly connected to the handle, or with one of the blades completely removed from the handle without removing the entire speculum from the patient's vagina. The speculum can be provided with means for protecting the interior of the front parts of the handle from penetration of vaginal discharge, or the like.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, a locking mechanism for blades 24 and 26 may be different from the snapping mechanism shown and described in the specification. For example, it can be a spring-loaded ball in the handle part that could snap into the recess or opening of the blade. One of the overlapping edges 80 and 82 may telescopically enter a recess in the other edge. The set of blades may contain the attachable blades of a small, medium, and large size, small and large size, etc. The blades may have slightly different configurations and even different connection elements, provided that these connection elements able to secure the blade due to engagement with the dimple or opening on the handle. The detent can be formed on the inner surface of the handle part, and the dimple or opening can be formed on the proximal end of the blade. The blades can be made from metal, or other materials. The principle of the invention is applicable not only to a vaginal speculum with a composite disassembled handle but also to a speculum with a monolithic handle that can interact with removable and sliding blades.

What we claim is:

1. A vaginal speculum comprising:
    a handle portion having a proximal end and a front part; and
    at least one pair of attachable blades removably attachable to said front part of said handle portion and a pair of sliding blades slidingly insertable into said proximal end of said handle portion; said at least one pair of attachable blades never being present in the handle portion simultaneously with the pair of sliding blades said sliding blades comprises a first sliding blade and a second sliding blade;
    said first sliding blade having engagement means for snapping engagement with said means for disconnectable attachment of said first attachable blade to said first handle part; and
    said second sliding blade having engagement means for snapping engagement with said means for disconnectable attachment of said second attachable blade to said second handle part;

said handle portion comprising a first handle part and a second handle part, said first handle part having a proximal end and a front part, and said second handle part having a proximal end and a front part;

said attachable blades comprising a first attachable blade and a second attachable blade;

said front part of said first handle part having means for disconnectable attachment of said first attachable blade to said front part of said first handle part;

said front part of said second handle part having means for disconnectable attachment of said second attachable blade to said front part of said second handle part;

each of said first attachable blade and said second attachable blade having a distal end and a proximal end, said proximal end of each of said first attachable blade and said second attachable blade being made in the form of a protective hood over the front part of the handle in order to prevent contact of said front part of the handle with vagina when said at least one pair of attachable blades removably attachable to said front part of said handle portion is inserted into the patient's vagina.

2. The vaginal speculum of claim 1, wherein said vaginal speculum is provided with a plurality of said attachable blades of different width and length that are removably attachable to said front part of said handle.

3. The vaginal speculum of claim 1, wherein said means for disconnectable attachment of said first attachable blade to said front part of said first handle part comprise a first snapping mechanism that secures said proximal end of said first attachable blade to said front part of said first handle part when said proximal end of said first attachable blade is fitted onto said front part of said first handle part and is shifted linearly in the direction of said handle; said means for disconnectable attachment of said proximal end of said second attachable blade to said front part of said second handle part comprise a second snapping mechanism that secures said proximal end of said first attachable blade to said front part of said second handle part when said proximal end of said second attachable blade is fitted onto said front part of said second handle part and is shifted linearly in the direction of said handle.

4. The vaginal speculum of claim 3, wherein said first snapping mechanism comprises an opening in one of said front part of said first handle part and said proximal end of said first attachable blade and a first detent on the other of said front part of said first handle part and said proximal end of said first attachable blade, and wherein said second snapping mechanism comprises an opening in one of said front part of said second handle part and said proximal end of said second attachable blade and a second detent on the other of said front part of said second handle part and said proximal end of said second attachable blade.

5. The vaginal speculum of claim 4, wherein said proximal end of said first attachable blade comprises a first inner semicircular portion and a first outer semicircular portion which is concentric with respect to the said first inner semicircular portion, said first detent being formed on said first inner semicircular portion, and said opening being formed on said first outer semicircular portion, and wherein said proximal end of said second attachable blade comprises a second inner semicircular portion and a second outer semicircular portion which is concentric with respect to the said second inner semicircular portion, said second detent being formed on said second inner semicircular portion; when said proximal end of said first attachable blade being attached to said front part of the first handle part, said front part of said first handle part being telescopically inserted between said first outer semicircular portion and said first inner semicircular portion, and when said proximal end of said second blade being attached to said front part of the second handle part, said front part of said second handle part being telescopically inserted between said second outer semicircular portion and said second inner semicircular portion.

6. The vaginal speculum of claim 5, wherein said first detent is spring-loaded and wherein said second detent is spring-loaded.

7. The vaginal speculum of claim 1, wherein at least said sliding blades have measurement scales.

8. The vaginal speculum of claim 4, wherein at least said sliding blades have measurement scales.

* * * * *